(12) United States Patent
Farin

(10) Patent No.: US 6,302,881 B1
(45) Date of Patent: Oct. 16, 2001

(54) METHOD AND APPARATUS FOR THE REMOVAL OF SMOKE DURING HIGH-FREQUENCY SURGERY

(75) Inventor: Günter Farin, Tübingen (DE)

(73) Assignee: Erbe Elektromedizin GmbH, Tubingen (DE)

( * ) Notice: Subject to any disclaimer, the term of this patent is extended or adjusted under 35 U.S.C. 154(b) by 0 days.

(21) Appl. No.: 09/470,862

(22) Filed: Dec. 23, 1999

(30) Foreign Application Priority Data

Dec. 29, 1998 (DE) .............................................. 198 60 689

(51) Int. Cl.⁷ .................................................. A61B 18/18
(52) U.S. Cl. .................. 606/41; 606/34; 606/38; 606/45; 604/35
(58) Field of Search ................... 604/35; 606/34, 606/38, 41, 45, 46, 49

(56) References Cited

U.S. PATENT DOCUMENTS

| 5,108,389 | 4/1992 | Cosmescu . |
| 5,160,334 | 11/1992 | Billings et al. . |
| 5,318,516 | 6/1994 | Cosmescu . |
| 5,620,441 | 4/1997 | Greff et al. . |
| 5,674,219 | 10/1997 | Monson et al. . |
| 5,836,909 | * 11/1998 | Comescu .............................. 606/28 |
| 5,951,548 | * 9/1999 | DeSisto et al. ....................... 606/42 |

FOREIGN PATENT DOCUMENTS

| 25 04 280 A1 | 2/1975 | (DE) . |
| 0 219 68 A1 | 10/1985 | (EP) . |

* cited by examiner

*Primary Examiner*—Linda C. M. Dvorak
*Assistant Examiner*—David M. Ruddy
(74) *Attorney, Agent, or Firm*—Marshall, O'Toole, Gerstein, Murray & Borun

(57) ABSTRACT

During the treatment of biological tissues by high-frequency surgery, contaminants, in particular smoke, are produced. In the present invention a suction device for removal of the contaminants is controlled in such a way that it becomes active only when a voltage sufficient to ignite an arc exists at an applicator of the HF-surgery device, and/or an arc is burning between the applicator and the treatment region, and/or the treatment region reaches a temperature at which smoke can be produced.

15 Claims, 1 Drawing Sheet

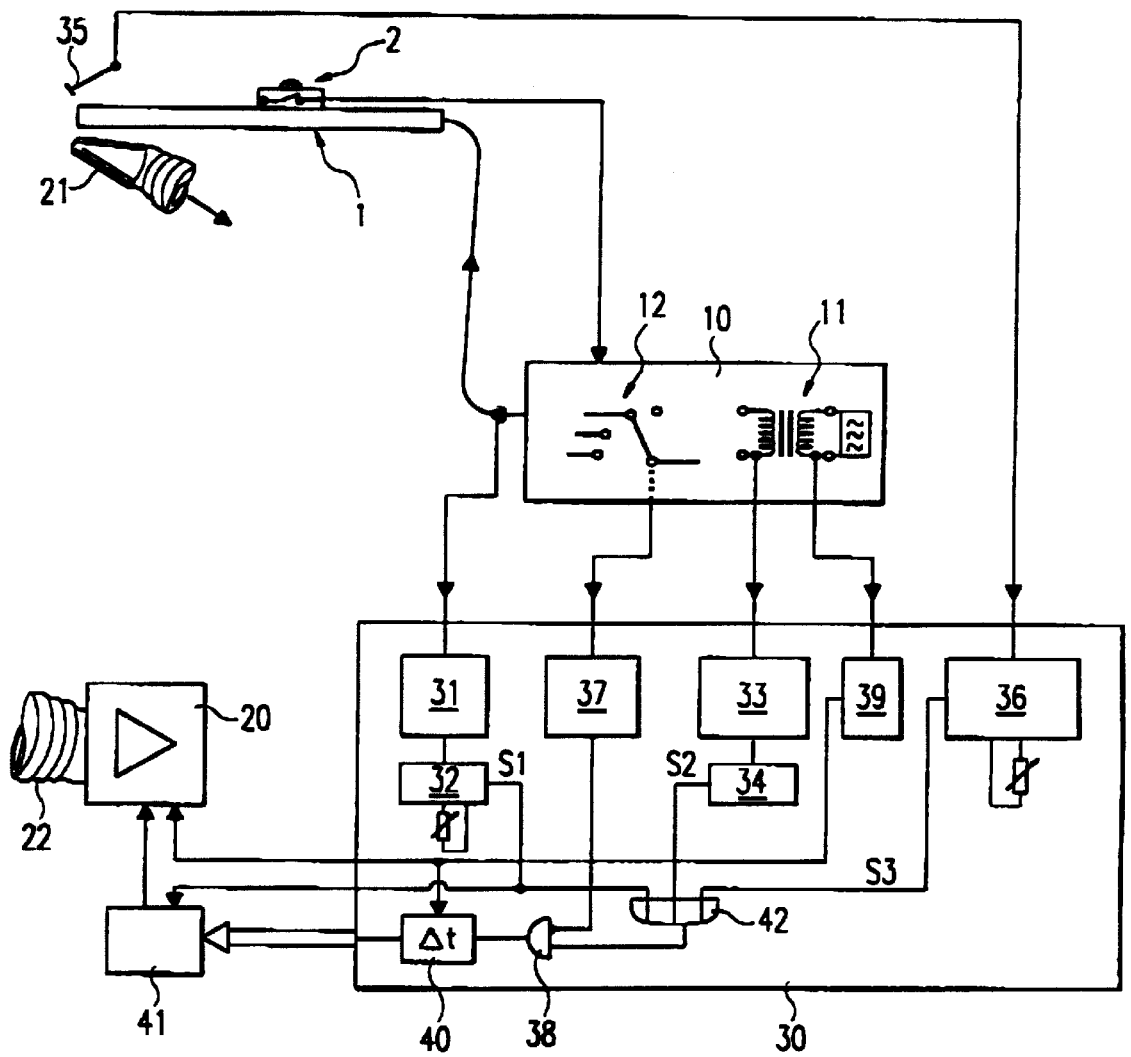

METHOD AND APPARATUS FOR THE REMOVAL OF SMOKE DURING HIGH-FREQUENCY SURGERY

FIELD OF THE INVENTION

The present invention relates to a method and an apparatus for the removal of smoke or similar interfering contaminants that are produced during the treatment of biological tissue by high-frequency surgery.

DESCRIPTION OF THE PRIOR ART

A method and an apparatus of this kind are known, for example, from the U.S. Pat. Nos. 5,160,334; 5,620,441; 5,108,389; 5,318,516. In these documents it is proposed to suck away smoke or water vapor during HF surgery or laser operations in order, first, to prevent contamination of nearby tissue, which could lead to postoperative problems, and, in general, to remove whatever interfering vapors impair visibility.

A particular problem with the known methods and apparatus resides in the fact that the associated suction equipment generates unpleasant noises, like those of a vacuum cleaner, which are extremely disturbing in an operating theater. Furthermore, it is desirable in operating theaters to have as few electrical devices running as possible, because they can cause electrical or electromagnetic interference.

The object of the present invention is to provide a method and an apparatus for the removal of smoke or similar interfering contaminants that are produced during the treatment of biological tissue by high-frequency surgery wherein the aforemnentioned disturbances are substantially reduced in a simple manner.

SUMMARY OF THE INVENTION

According to a first aspect of the present invention there is provided a method for the removal of contaminants that are produced during the treatment of biological tissue by high-frequency surgery using an HF-surgery device comprising an applicator through which the device transmits an electrical output to a treatment region of the tissue;

a controllable suction device for the removal of contaminants in the immediate vicinity of the applicator; and a control mechanism to control the suction device dependent on an operating state of the HF-surgery device; and wherein the method comprises the steps of generating a control signal when at least one of the following operational states exists:

(a) a voltage at the applicator suffices to ignite an arc;
(b) an arc exists between the applicator and the tissue; and
(c) a temperature in the treatment region exceeds a predetermined temperature; and activating the suction device when the control signal is turned on; and deactivating the suction device when the control signal is turned off.

Hence the removal of contaminants by suction begins only when interfering contamination (in particular by smoke) can in fact occur. Thus the route followed here is completely different from the state of the art, because in all known devices for this purpose the smoke suction begins as soon as activation of the devices or dissection instruments is initiated, and is thus independent of whether smoke or vapor can indeed be produced or not.

Thus in accordance with the present invention a control signal is generated when one or more of the following operating states prevails:

the voltage at the applicator is sufficient to ignite an arc;
an arc exists between the applicator and the tissue; and
the temperature of the region being treated exceeds a predetermined temperature value, in particular 100° C. Depending on the control signal, the suction device is activated or inactivated.

In the first case, i.e. when a voltage is used that is sufficient to ignite an arc, the smoke suction is, so to speak, activated at the earliest possible time, whenever it is certain that when the applicator is brought up to the tissue smoke or vapor will be produced.

In the second case, i.e. when an arc in fact exists between the applicator and the tissue, the suction is turned on only if contaminating substances, specifically smoke, are produced. While the HF voltage between applicator and tissue is below this critical level, no arc or spark and hence no smoke can come into existence, but vapor can be produced if the device for coagulation is used with direct contact at the electrode. In this case however, as mentioned, the smoke extraction mechanism is not turned on.

In the third case in which the suction is turned on when the temperature of the region being treated exceeds a predetermined level, vapor is sucked away when the temperature is in the region of about 100° C. To ensure that the suction process occurs only when smoke is present, the temperature threshold can be set higher, i.e. above 100° C., because at lower temperatures no smoke can be produced. As a result of the characteristics cited above, to be used alternatively or cumulatively, it is ensured that the process of smoke extraction is activated as rarely as possible.

Preferably, the control signal that initiates smoke extraction is suppressed when the device for HF surgery is in an operating mode in which no smoke can be produced, in particular when an inert or noble gas, especially Ar or He, is being applied to the treated region. In this case all three of the above-mentioned criteria (ignition voltage, arc, temperature level) can be met without the production of smoke. The reason is that in the presence of an inert gas no oxygen is available, so that the tissue is reliably prevented from burning and hence producing smoke.

The performance of the suction device is preferably controlled in such a way that when the electrical power is increased, the suction is made stronger. This feature ensures that the noise or interference level of the suction device is kept as low as possible, while at the same time the strength of suction can be adjusted to produce an adequate effect.

The control signal is preferably maintained for a predetermined period of time after the first or second operating state (temperature, arc) has ended, in order to ensure that any smoke or vapor produced will be completely extracted.

In another preferred embodiment the suction device is brought to a lower, initial power level when an arc-ignition voltage is present between the applicator and the tissue, until either an actual arc or an increased temperature is detected; then these in turn cause the suction strength to be increased. By this means it is ensured that whenever the surgeon operates the actuating mechanism (pedal, button on applicator) in order to cut or coagulate tissue, the suction device is already put into an activated state so that when smoke or vapor in fact appears, it is immediately able to remove it with stronger suction, a performance level that can be reached more readily and rapidly from the initial, lower-power state than from a completely deactivated state.

To implement this method and in accordance with a second aspect of the present invention there is provided apparatus for the removal of contaminants that are produced during the treatment of biological tissue by HF-surgery comprising an HF-surgery device;

an applicator through which the device transmits an electrical output to a treatment region of the tissue;

a controllable suction device for the removal of contaminants in the immediate vicinity of the applicator; and a control mechanism to control the suction device dependent on an operating state of the HF-surgery device; and wherein the improvement comprises the provision of at least one of (a) a first monitoring means to detect a voltage at the applicator; and a first comparator in the control mechanism to compare the voltage with a predetermined ignition-voltage value and to send out a first control signal for the activation of the suction device whenever the voltage reaches at least the ignition-voltage level; and (b) a second monitoring means to detect an operating state of the HF-surgery device and to send out an operating-state signal; and a recognition device in the control mechanism to receive the operating-state signal and to send out a second control signal for the activation of the suction device whenever, on the basis of the operating-state signal, the existence of an arc between the treatment region and the applicator is recognized; and (c) a third monitoring means to detect at least one of a temperature of the treatment region and the presence of electromagnetic radiation originating from the treatment region; and a second comparator in the control mechanism to compare the level of at least one of the detected temperature and the detected electromagnetic radiation respectively with a predetermined temperature level and a predetermined radiation level and to send out a third control signal for the activation of the suction device whenever the detected level exceeds the predetermined level.

The second monitoring means can be substantially constructed as is described for example in the patents DE 25 04 280 or EP0219 568, to which reference is made explicitly here.

The third monitoring means preferably detects the emission of radiation, which can comprise infrared radiation as well as visible light. Thus with this third monitor it can be determined whether the treatment region is at a temperature such that vapor or smoke can be produced (sampling of thermal radiation), or whether an arc is present. In the last case it is necessary to monitor a relatively large angle, because the exact site to which the arc migrates is usually not strictly specifiable.

Preferably an operating-mode detector is provided in order to determine the momentary operating mode of the instrument for HF surgery. Dependent on this operating mode, the control signal to turn on the suction device is either "switched through" or suppressed. Suppression occurs in particular when the selected operating mode is such that no smoke or visibility-impairing vapor can be produced. This is the case especially when the instrument for HF surgery is emitting a noble gas (He, Ar) onto the treatment region, so that the arc burns in the noble gas and the treatment region is kept free from oxygen.

In addition, a power-monitoring means is preferably provided, which determines the electrical power being applied to the treatment region by the instrument for HF surgery. Dependent on this power, an adjustment signal is generated that controls the suction strength of the suction device in such a way that when the electrical power is relatively high, the suction strength is higher than when the electrical power is relatively low. This measure ensures that when only low electrical power is being used, so that only slight smoke is produced, the suction is set to a lesser strength and hence less interference is produced.

Preferably a delay means is provided that delays switching off of the suction device for a predetermined period of time after the second or the third control signal is turned off, i.e. after an arc is extinguished or the temperature of the treatment region (radiation from the treatment region) has fallen below a predetermined level. As a result, it is ensured that remnants of smoke continue to be extracted so that no contamination of the treatment region can occur. In this case the delay device is preferably adjustable, with respect to the switch-off delay it produces, in such a way that when there is an increase in the electrical power or in the length of time during which a predetermined minimal power is exceeded (or an arc is burning), the delay is adjusted accordingly. As a result, it is likewise ensured that increased amounts of smoke are reliably extracted.

In order to ensure that as soon as possible after the onset of vapor or smoke development the suction is working efficiently, in addition an initial-power control device is provided which, when the first control signal is received, sets the suction device to a relatively low initial power, and when the second or third control signal is present, resets it to a higher suction strength. That is, the suction device is already put into operation when a voltage in principle capable of ignition is present, which is the case as soon as the instrument is actuated (finger or foot switch). From this lower initial-power level, a transition to a higher suction strength can the n be made very rapidly.

It is advantageous to use the invention in connection with HF surgery in the endoscopic area of application. The reason is that when smoke is produced within a body cavity, the risk of contamination is particularly high. Furthermore, the smoke is also particularly disturbing in this situation, so that efficient smoke extraction is particularly helpful. Finally, it should also be mentioned that smoke (as well as vapor) can dirty the optics of the endoscope and thus make the operation difficult. Surprisingly, therefore, the extraction of smoke by suction has proved to be especially desirable for endoscopic operations.

BRIEF DESCRIPTION OF THE DRAWINGS

The various aspects of the present invention will now be described by way of example with reference to the accompanying drawing which is a schematic block diagram of an apparatus for HF surgery with a control mechanism.

DESCRIPTION OF THE PREFERRED EMBODIMENT

In this exemplary embodiment an HF-surgery device, identified by the reference numeral 10, comprises a high-frequency power generator 11 and adjustment elements 12 by means of which the operating modes of the instrument are selected, e.g. the modes "cutting", "coagulation", "APC" (argon-plasma coagulation) and the like. The HF-surgery device 10 is connected in a conventional manner to an applicator 1, by means of which the HF output may be brought to the region of a biological tissue that is to be treated. Preferably the applicator 1 is so designed that it can be used for endoscopic operations; that is, it can be passed through the working channel of an endoscope.

In addition an actuating means 2 is provided, by way of which the HF-surgery device can be actuated by the operator. In this exemplary embodiment the actuating means 2 is constructed as an operating button or key mounted on the applicator 1. In the case of an applicator for endoscopic operations, this actuating means may take the form, for example, of a pedal.

In order to extract vapor or smoke a suction device 20 is provided, which is connected by way of a suction tube 22 to a nozzle 21 mounted on the applicator. The nozzle 21 is so disposed that its opening is as close as possible to the site from which the interfering contaminants are to be sucked away.

A control mechanism 30 is provided to turn on the suction device 20. The control mechanism 30 comprises an ignition-voltage monitor 31, which detects the voltage present at the applicator 1 or generated by the HF-surgery device 10. The site at which the voltage is monitored is indicated schematically in the drawing on the output lead from the HF-surgery device to the applicator 1; however, what will be used in practice is always a signal generated by the HF-surgery device 10 that is proportional to the actual ignition voltage. The voltage detected by the ignition-voltage monitor 31 in the control mechanism 30 is compared, by means of a first comparator 32, with a predeterminable voltage corresponding to an ignition voltage that is necessary, in particular during cutting, to ignite a spark or arc. Thus as soon as this voltage is detected, the possibility exists that a cutting process is in fact being initiated in which smoke can be produced. At lower voltages no smoke, but at most water vapor, can appear. The first comparator 32 generates a control signal S1.

In addition an operating-state monitor 33 is provided, which detects the operating state of the HF-surgery device 10 and which is connected to a recognition device 34. The latter is so designed that a second control signal S2 is sent out when the recognition device 34 recognizes, from the output signal of the operating-state monitor 33, that an arc is burning between the applicator 1 and the treatment region. A recognition device of this kind is described, for example, in the patents DE2504280 or EP 0 219 568.

Furthermore, a temperature monitor 35 is provided at the applicator 1, which for example can be constructed as a pyrometer or as a receiver for visible light, in order to determine the temperature of the treatment region or light emission in this region (e.g., when a spark is produced). The output signal of the temperature monitor 35 is sent to a second comparator 36, in which it can be compared with a predeterminable value so that when the latter is exceeded, a third control signal S3 is generated, namely when the temperature of the treatment region is so high that smoke can be produced.

In the control mechanism 30 there is further provided an operating-mode detector 37, which detects the operating mode of the HF-surgery device by monitoring the setting of the adjustment elements 12. Whenever the operating-mode detector 37 determines that the HF-surgery device 10 is in an operating mode such that no contaminants, in particular smoke, are produced, for instance in the operating mode "APC", it sends a suppression signal to a suppression means 38, which in the present case is constructed as an AND gate with one inverting input.

The control signals S1, S2 and S3 are sent to an OR gate 42, the output of which is connected to the non-inverting input of the AND gate 38. The output of the AND gate is sent to the input of a delay device 40, which sends a control signal through an initial-power controller 41 to the suction device 20 in order to start the operation of the latter. In this embodiment of the invention, therefore, whenever one of the control signals S1 to S3 is present and the operating mode of the HF-surgery device is such that contaminants can be produced, the suction device 20 is turned on. When the three control signals S1, S2 or S3 are no longer present, the delay device 40 causes the suction device 20 to be turned off after a certain delay, so as to ensure that remnants of the contaminating substances are sucked away from the region between the biological tissue and the applicator 1.

In addition an output monitor 39 is provided, which generates a signal corresponding to the effective power generated by the HF-surgery device 10. This signal is sent both to the delay device 40 and to the suction device 20. On the basis of this output-dependent signal, in the delay device 40 the delay time is lengthened or shortened so that when the output of the HF-surgery device is higher, the suction is continued for a longer period after the surgical procedure has stopped than when its output is lower. This measure ensures that when more of the contaminants are being produced, especially smoke, the smoke that has been produced will be sucked away even after the cutting process has been ended. Alternatively or in addition, the delay duration can be influenced by the time during which the HF-surgery device has been generating, and hence sending to the tissue, any output at all. Then the duration of suction after the surgical procedure corresponds not to the output in terms of power but to the energy generated by the HF-surgery device.

The signal corresponding to the power is also sent directly to the suction device 20, so that during a high-powered cutting operation the suction strength is also greater than when the HF power is lower.

From the above it will be evident that in the present invention the suction device is actuated dependent on parameters related to the energy generated by the HF-surgery device, which is substantially directly responsible for the production of contaminants, in particular smoke but also vapor. In this way the forms of interference associated with the suction process can be minimized while at the same time the efficiency of suction can be maintained or even enhanced.

What is claimed is:

1. Method for the removal of contaminants that are produced during the treatment of biological tissue by high-frequency surgery using an HF-surgery device comprising
    an applicator through which the device transmits an electrical output to a treatment region of the tissue;
    a controllable suction device for the removal of contaminants in the immediate vicinity of the applicator; and
    a control mechanism to control the suction device dependent on an operating state of the HF-surgery device; and wherein the method comprises the steps of
    generating a control signal when at least one of the following operational states exists:
        (a) a voltage at the applicator suffices to ignite an arc;
        (b) an arc exists between the applicator and the tissue; and
        (c) a temperature in the treatment region exceeds a predetermined temperature; and
    activating the suction device when the control signal is turned on; and
    deactivating the suction device when the control signal is turned off.

2. Method as claimed in claim 1, wherein the control signal is suppressed when the HF-surgery device is in an operating mode in which no smoke can be produced.

3. Method as claimed in claim 1, wherein the control signal is suppressed when the HF-surgery device is operating to send an inert gas to the treatment region.

4. Method as claimed in claim 1, wherein the suction strength of the suction device is controlled in such a way that when more electrical power is being generated the suction strength is increased.

5. Method as claimed in claim 1, wherein the control signal is maintained on for a predetermined period of time after one of the operating states (b) and (c) has been terminated.

6. Method as claimed in claim 4, wherein when the operating state (a) exists in the absence of one of the operating states (b) and (c), the suction strength of the suction device is set at a low initial power level, and when there is a subsequent transition into one of the operating states (b) and (c) the suction strength is increased.

7. Apparatus for the removal of contaminants that are produced during the treatment of biological tissue by HF-surgery according to the method as claimed in claim 1, comprising an HF-surgery device;

an applicator through which the device transmits an electrical output to a treatment region of the tissue;

a controllable suction device for the removal of contaminants in the immediate vicinity of the applicator; and a control mechanism to control the suction device dependent on an operating state of the HF-surgery device; and wherein the improvement comprises the provision of at least one of (a) a first monitoring means to detect a voltage at the applicator; and a first comparator in the control mechanism to compare the voltage with a predetermined ignition-voltage value and to send out a first control signal for the activation of the suction device whenever the voltage reaches at least the ignition-voltage level; and (b) a second monitoring means to detect an operating state of the HF-surgery device and to send out an operating-state signal; and a recognition device in the control mechanism to receive the operating-state signal and to send out a second control signal for the activation of the suction device whenever, on the basis of the operating-state signal, the existence of an arc between the treatment region and the applicator is recognized; and (c) a third monitoring means to detect at least one of a temperature of the treatment region and the presence of electromagnetic radiation originating from the treatment region; and a second comparator in the control mechanism to compare the level of at least one of the detected temperature and the detected electromagnetic radiation respectively with a predetermined temperature level and a predetermined radiation level and to send out a third control signal for the activation of the suction device whenever the detected level exceeds the predetermined level.

8. Apparatus as claimed in claim 7, comprising an operating-mode detector that identifies an operating mode of the HF-surgery device and that produces an output signal whenever the HF-surgery device is in an operating mode in which no smoke can be produced, and a suppression means that suppresses the control signal on receipt of the output signal from the operating-mode detector.

9. Apparatus as claimed in claim 7, comprising an operating-mode detector that identifies an operating mode of the HF-surgery device and that produces an output signal whenever the HF-surgery device is in an operating mode in which an inert gas is being supplied to the treatment region, and a suppression means that suppresses the control signal on receipt of the output signal from the operating-mode detector.

10. Apparatus as claimed in claim 7, comprising a power-monitoring means that detects the electrical power generated by the HF-surgery device and that outputs an adjustment signal to control a suction strength of the suction device in such a way that when the electrical power being generated is set at a high level the suction strength is higher than when the electrical power being generated is set at a lower level.

11. Apparatus as claimed in claim 7, comprising a delay means for delaying a turning off of the suction device for a predetermined period of time after one of the second and third control signals have been turned off.

12. Apparatus as claimed in claim 11, wherein the delay means comprises an adjustment means that increases the predetermined period of time as the electrical power generated by the HF-surgery device increases.

13. Apparatus as claimed in claim 11, wherein the delay means comprises an adjustment means that increases the predetermined period of time as the time during which HF-surgery device is in operation generating an electrical power output above a predetermined minimal level increases.

14. Apparatus as claimed in claim 7, comprising an initial-power controller that sets the suction strength of the suction device to a relatively low initial power level in the presence of the first control signal and that resets the suction strength to a higher level when at least one of the second and third control signals is present.

15. Apparatus as claimed in claim 7, for use in the removal of smoke by suction wherein the applicator is adapted for use in endoscopic treatments.

\* \* \* \* \*